United States Patent [19]

Becker

[11] Patent Number: 4,790,309
[45] Date of Patent: Dec. 13, 1988

[54] TISSUE EXPANDER STENT

[76] Inventor: Hilton Becker, 2584 NW. 23rd Way, Boca Raton, Fla. 33413

[21] Appl. No.: 36,800

[22] Filed: Apr. 10, 1987

[51] Int. Cl.$^4$ ............................................. A61B 17/00
[52] U.S. Cl. .............................. 128/303 R; 128/334 R
[58] Field of Search .................. 128/343, 150, 334 R, 128/303 R

[56] References Cited

FOREIGN PATENT DOCUMENTS

| 273631 | 4/1930 | Italy | 128/150 |
| 17675 | 10/1916 | United Kingdom | 128/150 |

Primary Examiner—Michael H. Thaler
Attorney, Agent, or Firm—Bacon & Thomas

[57] ABSTRACT

The disclosure relates to a tissue expander/stent or splint for use by a plastic surgeon in the reconstruction of a nipple in a human breast and to a method for splinting a reconstructed nipple. The stent is made of soft pliable material and defines a generally frusto conically shaped segment with a short cylindrical tubular element extending outwardly therefrom. The stent also includes a rigid ring which is encompassed by the tubular element.

The method of splinting includes the steps of forcing the conical segment downward onto the breast, and suturing the reconstructed nipple to the stent so that the resiliency of the conical segment maintains the sutures under tension and tends to pull the nipple upwardly during healing.

3 Claims, 1 Drawing Sheet

TISSUE EXPANDER STENT

BACKGROUND OF THE INVENTION

This invention relates to an improved tissue expander and stent for use in the reconstruction of a nipple in a human breast and to a method for splinting the reconstructed nipple.

Over the last few years, nipple-areola reconstruction in female patients has been greatly improved by new surgical techniques. And today, the surgeon is able to reconstruct a symmetrical areolar complex with an excellent projecting nipple. For example, the subcutaneous pedicle technique with splinting can be used to produce an extremely natural appearing nipple which remains elevated about 1 cm. above the areola. Such procedures have been described, for example, by Dale B. Dubin, M.D. in an as yet unpublished article, "A New Simplified Method for Nipple Reconstruction," a copy of which is being provided to the examiner. That procedure and the splint disclosed by Dubin are described below.

In performing these surgical procedures, a surgeon makes a circular incision in the breast, places a rigid or semi-rigid tubular splint on the breast with the circular incision surrounded by the tubular splint. The patient's tissue expands upwardly into the tubular splint and the flap of skin, i.e. the skin which covers the area of tissue within the circular incision, is sutured to the splint. The splint is then left in place for a period of two (2) or more weeks. Then after healing, the stitches and splint are removed.

Dubin disclosed the use of a circular cap from the container of a 35 cc Monoject disposable syringe (obtained from Monoject of St. Louis, MO) as a stent. The center of the flat portion of the relatively rigid cap was cut out with a hot tip cautery. Then four vertical 4 mm slits were made with a #15 blade every 90° along the edge of the plastic cap. The flat side of the modified cap was then placed on the breast of a patient with the reconstructed nipple extending upwardly through the hole and with the circular portion of the cap extending upwardly from the breast and surrounding the nipple. Four nylon sutures placed just below the dermis of the nipple were brought through the hole in the cap before the cap was placed on the patient's breast. The nipple was pulled vertically and the nylon sutures were secured in the slits along the edge of the cap. The nylon sutures were then taped along the outside edge of the surrounding wall with adhesive tape.

The use of rigid tubular splints can cause patient discomfort and at times loss of tension in the sutures during the healing process. In addition, the small tubular splints may be relatively difficult to handle and position during surgery and do not promote tissue expansion to the degree desired.

An improved tissue expander and stent according to the present invention reduces patient discomfort and enhances tissue expansion. In addition, the stent is easier to position and suture in place, and therefore facilitates the surgical techniques.

The improved tissue expander and stent disclosed herein is made of soft, pliable and resilient material, is readily sutured in place, and at the same time reduces or eliminates any likelihood of the sutures being pulled through the soft pliable material without adding to the patient's discomfort.

In addition, the improved stents disclosed herein can be manufactured at a relatively low cost, are readily sterilized and can be readily packaged and shipped in a sterile condition.

SUMMARY OF THE INVENTION

The present invention relates to an improved tissue expander and stent for use in the reconstruction of a nipple in a human breast. The tissue expander and stent is made of a soft, pliable and resilient material such as a silicone elastomer and therefore reduces in so far as possible any discomfort to a patient. In essence, the tissue expander stent includes a soft, pliable and resilient member which defines a hollow radially flared annular of generally frusto conically shaped segment and a cylindrical tube. The cylindrical tube extends upwardly and outwardly from the top of the frusto conical segment and is formed integrally therewith. A rigid ring preferably of stainless steel is encompassed by the cylindrical tube at the distal end thereof.

In a preferred embodiment of the invention, the rigid ring is slipped or forced over the cylindrical tube and the end of the tube is folded or rolled over the ring and worked or extended down toward to the top region of the conical segment forming a double walled tube with the rigid ring encompassed by the tube at the distal end thereof. This structure is then readily attached to human tissue with sutures that pass through the relatively soft tubular portion and around the rigid ring. The rigid ring then prevents the sutures from being pulled through the soft material without adding to the discomfort of the patient.

The invention also contemplates a method for splinting a reconstructed nipple to enhance the tissue expansion thereof. The method includes the following steps:

(a) providing a stent expander as described above;

(b) placing the stent expander on the breast and over the area of nipple reconstruction so that the proximal end of the tubular element is at least several millimeters above the area of reconstruction;

(c) forcing the conical segment downward against the breast; and (d) suturing the distal end of the tube to an area of skin that has been forced upward after a surgeon makes a circular incision; and (e) maintaining tension on the sutures by the resiliency of the stent so that the nipple portion is pulled upwardly to thereby enhance tissue expansion.

DESCRIPTION OF THE PREFERRED EMBODIMENT

Figure 1:
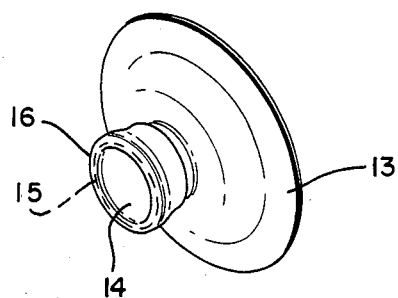
FIG. 1 is a perceptive view which illustrates an improved tissue expander stent according to a preferred embodiment of the present invention.
Figure 2:
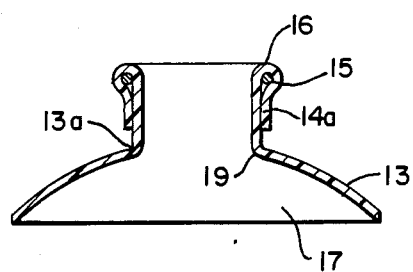
FIG. 2 is a cross-sectional view of the tissue expander stent which is shown in FIG. 1.

Reference will now be made to the preferred embodiment of the invention which is illustrated in the accompanying drawings.

A preferred embodiment of an improved tissue expander stent is shown in FIGS. 1, 2, 4 and 5 In accordance with the invention and as embodied herein, the tissue expander stent, or splint as it is sometimes referred to, is made of soft, pliable and resilient material such as a silicone elastomer.

The silicone elastomer can be readily sterilized and while soft and pliable has sufficient body or rigidity to maintain its shape. In addition, it has sufficient resiliency to exert a slight tension on the sutures as will be described below.

The improved stent is made of a soft, pliable and resilient material and defines a hollow or concave generally frusto conical segment 13 and a cylindrical tube or element 14. The cylindrical tube 14 has the shape of a right circular cylinder and extends outwardly or upwardly from a top portion 13a of the frusto conical segment 13 and is formed integrally therewith.

A rigid ring 15 is preferably made of stainless steel or some other readily sterilizable material which is suitable for medical applications as will be readily understandable by those who are skilled in the art. The ring 15 is encompassed by the cylindrical tube 14 at the distal end 16 thereof and prevents the tube from collapsing inwardly.

The shape of the stent can be defined as a hollow or concave generally frusto conical segment 13 with a right circular tubular element 14 extending outwardly from the top is adjacent to the outer wall of the conical segment and forms an extension thereof. However, it should be understood that the walls or surface of the conical segment 13 may be flat or curved.

And, in the preferred embodiment of the invention, the outside diameter of the base 17 of the generally frusto conical segment 13 is between about 1 ½ to about 1 ¾ inches, and the inside diameter of the tubular element 14 is between about ⅜ and about ½ inches. The height of the conical segment is approximately ¼ to ⅜ inches and the distal end 16 of the integral tube 14 is approximately ⅝ inches above the base 17 of the conical segment in its natural state of relaxation. In addition, the conical walls of the segment define an angle of between about 15° to about 45° with respect to the base.

In a preferred embodiment of the invention, the integral tube 14 is approximately ¾ inches in length. Then when the ring 15 is slipped over the tube 14, so that the ring 15 closely surrounds the tube 14, the end 14a is folded or rolled over the ring 15 and forced down to a position which is adjacent to the top of the conical segment as shown more fully in FIG. 2. As illustrated therein, walled tube 14. The length of the folded cylindrical tube 14 can be adjusted by changing the position of ring 15.

In reconstruction of the nipple-areola area, the surgeon may use intradermal tattooing as described in applicant's article on "The Use of Intradermal Tattoos to Enhance the Final Result of Nipple-Areola Reconstruction" in Plastic and Reconstructive Surgery, April 1986.

Figure 3:
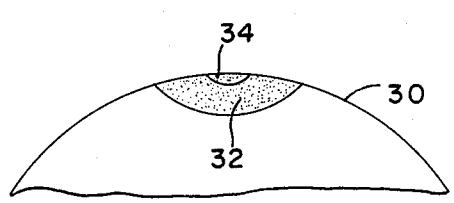
FIG. 3 is a side elevational view of a patient's breast in an initial stage of nipple reconstruction.
Figure 4:
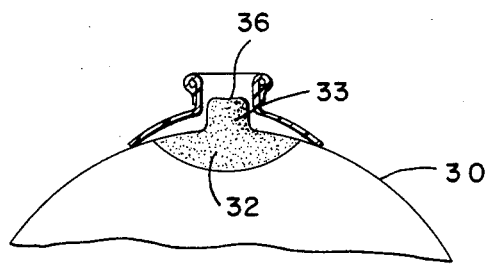
FIG. 4 is a side elevational view of a patient's breast after making an incision therein and after placing a tissue expander stent thereon.
Figure 5:
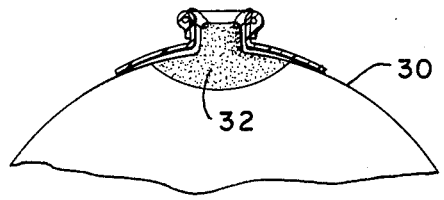
FIG. 5 is a side elevational view of a patient's breast with a tissue expander stent according to the present invention sutured in place.

With respect to FIGS. 3–5, a patient's breast 30 which may have been partially reconstructed, i.e. reconstructed without a nipple-areola, in the manner described in applicant's co-pending application no. 481,912 filed Apr. 4, 1983, now U.S. Pat. No. 4,643,733 and entitled Permanent Reconstruction Implant and Method of Performing Human Tissue Expansion is shown.

The breast 30 has an area 32 tattooed to resemble an areola. This tattooing is accomplished by using a multiple needle-type brush manufactured by Permark Corp. of Teaneck, N.J. 07666. And at the completion of the procedure, the wound is cleaned and Neosporin ointment and dressings are applied. Then after healing, a small circular incision 34 is made in the center of the areola and the underlying tissue 33 forces a skin flap 36 upwardly as illustrated more clearly in 1 FIG. 4. The skin flap 36 covers the area of tissue which is surrounded by the circular incision 34.

The base portion 17 of the generally frusto conical segment 13 is adjusted to have its concave portion placed over or on the breast 30 of a patient. The base portion 17 is placed on the breast, so that the proximal end 19 of the cylindrical tube 14 is elevated by at least several millimeters from the portion of the breast which is undergoing reconstruction.

The expander stent is placed on the breast after the surgeon makes the small circular incision at the site where he wants to construct a nipple as shown more clearly in FIGS. 4 and 5. And then, the edges of the skin flap 36 which lie within the circular incision are pushed upwardly by natural expansion and sutured to the top of the cylindrical tube 14.

In suturing the flap to the distal end 16, the surgeon forces the proximal end 19 of the tubular member downward toward the breast. The sutures are passed through the wall or double wall of tube 14 and around the rigid ring 15. Then the resiliency of the conical segment 13 maintains the sutures under tension without discomfort to the patient and enhances tissue expansion.

And because of the reduction in a patient's discomfort, there is less likelihood of a patient rubbing or bothering the reconstructed area during healing. In addition, the soft stent protects the area and reduces the likelihood of inflamation and therefore leads to healing.

Figure 6:
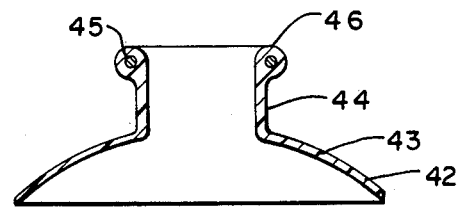
FIG. 6 is a cross-sectional view of an expander stent according to a second embodiment of the invention.

A second embodiment of the invention is illustrated in FIG. 6 and shows a molded stent having a generally frusto conically shaped segment 42 in which the walls 43 define a curved surface. In this embodiment the stent is molded as a one-piece construction with a tubular element 44 encompassing or surrounding a ring 45 at a distal end 46 of element 44.

Alternatively, although not presently preferred, a separate metal ring 45 in the suturing region of the tubular element 44 may be dispensed with and the distal end 46 may be molded as a thickened lip or ring. As a further alternative, tabs may be molded on the exterior of the distal end 46 of cylindrical element 44 for receiving the sutures.

It should be understood that the tubular element 44 can be molded as an integral part of the splint or fused to the generally frusto conical segment 42. However, from a practical standpoint it will be molded as a single piece.

It should also be understood that other materials can be substituted for the silicone elastomer provided that they are soft, pliable and have sufficient resiliency to maintain the sutures under tension.

The invention also contemplates a method of splinting a reconstructed nipple to enhance the tissue expansion thereof. The method includes the following steps:

a. A soft, pliable and resilient stent which defines a generally frusto conical segment and a cylindrical tubular element extending outwardly therefrom, and a rigid ring encompassed by the tubular element at the distal end thereof are provided;

b. The stent is placed on the breast in the area of nipple reconstruction with the base of the conical portion on the breast and the tubular element surrounding a small circular incision (about ⅜ inch in diameter) and with the proximal end of the tubular element elevated by at least several millimeters from the breast;

c. The stent is then forced gently downward against the breast to flatten the concave portion; and d. The distal end of the tubular portion is sutured to the flap of skin and underlying tissue which is surrounded by the circular incision by passing the stitches through the flap and around the rigid ring while holding the stent in a compressed state so that the resiliency of the stent maintains the sutures under tension and tends to lift the flap of skin and tissue thereunder upwardly during healing.

This tension is maintained as the reconstructed nipple heals.

While the invention has been described with respect to certain embodiments, it will be obvious that various modifications may be contemplated by those skilled in the art without departing from the scope of the invention as hereafter defined by the appended claims.

What is claimed is:

1. A tissue expander and stent for use in the reconstruction of a nipple in a human breast comprising a soft, pliable and resiliant member of a biologically compatable non-porous elastomer defining a hollow radially flared annular segment and a cylindrical tube extending outwardly from the top of said segment and formed integrally therewith, and a rigid ring encompassed by the cylindrical tube at the distal end thereof, said conically shaped radially flared annular segment defining a hollow base portion for placement on the breast of a patient so that the proximal end of said tube is elevated by at least several millimeters from the portion of the breast which is undergoing reconstruction, and said rigid forced over and closely surrounding said cylindrical tube and with said cylindrical tube folded over said ring and extending downwardly to the region of the top of said radially flared annular segment to thereby form a double walled tube with said ring at the distal end thereof, and the distal end of said tube is adapted to be sutured to said breast in a manner to force the proximal end downward against the breast whereby the resiliency of the radially flared annular segment maintains the suture under tension as the tissue expands upwardly into the interior of the tube.

2. A tissue expander and stent for use in the reconstruction of a nipple in a human breast comprising a soft, pliable and resilient member of a biologically compatible non-porous silicon elastomer defining a hollow radially flared annular segment and a cylindrical tube extending outwardly from the top of said segment and formed integrally therewith, and a rigid stainless steel ring encompassed by said cylindrical tube at the distal end thereof, and radially flared annular segment defining a concave base for placement on the breast of a patient so that the proximal end of said tube is elevated by at least several millimeters from the portion of the breast which is undergoing reconstruction, and said rigid ring forced over and closely surrounding said cylindrical tube and with said cylindrical tube folded over said ring extending downwardly to the region of top of said radially flared annular segment to thereby form a double walled tube with said ring at the distal end thereof, and the distal end of said tube is adapted to be sutured to said breast in a manner to force the proximal end downward against the breast whereby the resiliency of the concave base maintains the sutures under tension as the tissue expands upwardly into the interior of the tube.

3. A tissue expander and stent for use in the reconstruction of a nipple in a human breast according to claim 2 in which said conical segment has an outside diameter of between about 1 ½ to about 1 ¾ inches and a height of about ⅝ inches and in which said double walled tube has an inside diameter of between about ⅜ to about ½ inches and a length of about ⅝ inches and in which the conical wall forms an angle of about 15° to 45° with respect to its base.

* * * * *